(12) United States Patent
Kekäläinen et al.

(10) Patent No.: US 8,102,796 B2
(45) Date of Patent: Jan. 24, 2012

(54) WIRELESS DATA COMMUNICATION METHOD AND WIRELESS DATA COMMUNICATION SYSTEM

(75) Inventors: Panu Kekäläinen, Espoo (FI); Ossi Korhonen, Espoo (FI); Mikko Kaltto, Kalkkiranta (FI)

(73) Assignee: Wristop Technologies Oy, Turku (FI)

( * ) Notice: Subject to any disclaimer, the term of this patent is extended or adjusted under 35 U.S.C. 154(b) by 914 days.

(21) Appl. No.: 12/124,200

(22) Filed: May 21, 2008

(65) Prior Publication Data

US 2009/0290525 A1 Nov. 26, 2009

(51) Int. Cl.
*H04J 3/00* (2006.01)
*H04J 3/06* (2006.01)
*H04W 4/00* (2009.01)

(52) U.S. Cl. ......... 370/326; 370/336; 370/338; 370/350
(58) Field of Classification Search ........... 370/310–350
See application file for complete search history.

(56) References Cited

U.S. PATENT DOCUMENTS

| | | | |
|---|---|---|---|
| 6,640,268 B1 | 10/2003 | Kumar | |
| 6,807,159 B1 | 10/2004 | Shorey et al. | |
| 7,020,467 B2 * | 3/2006 | Tada | 455/434 |
| 7,085,256 B2 | 8/2006 | Ware et al. | |
| 7,653,017 B2 * | 1/2010 | Huylebroeck | 370/311 |
| 7,743,151 B2 * | 6/2010 | Vallapureddy et al. | 709/227 |
| 2003/0076842 A1 * | 4/2003 | Johansson et al. | 370/401 |
| 2011/0188434 A1 * | 8/2011 | Rhee | 370/311 |

FOREIGN PATENT DOCUMENTS

| | | | |
|---|---|---|---|
| EP | 1113690 A2 * | 7/2001 | |
| EP | 1560383 A2 * | 8/2005 | |
| WO | WO 2006017615 A1 * | 2/2006 | |

* cited by examiner

*Primary Examiner* — Tri H Phan
(74) *Attorney, Agent, or Firm* — Young & Thompson

(57) ABSTRACT

A method for transmitting and receiving data packets between a master device and at least one slave device using a synchronized data communication protocol. In the method, a time period to be used between consecutive packets to be transmitted to the master device is defined, on the basis of the calculated number of data packets received by the master device in a predetermined time period. In the wireless data communication system, a master device, and a slave device, including wireless data communication part transmit and receive data packets between the devices using a synchronized data communication protocol. In the protocol, the time period to be used between consecutive packets to be transmitted is defined on the basis of the calculated number of data packets received by the master device in a predetermined time period.

15 Claims, 2 Drawing Sheets

WIRELESS DATA COMMUNICATION METHOD AND WIRELESS DATA COMMUNICATION SYSTEM

FIELD OF THE INVENTION

The present invention relates generally to a system, including a wrist computer, for monitoring medical devices in a medical device network using a wireless data communication protocol.

More particularly, the present invention relates to systems and techniques related to a wireless data communication protocol, and wireless data communication features suitable for use in a medical device network environment.

BACKGROUND OF THE INVENTION

There are over 20 million people in the United States and tens of millions world wide, who have diabetes. Diabetes is a disease in which blood glucose levels are too high, and in which the body does not produce or properly use insulin, which is a hormone that is needed to convert sugar, starches and other food substance into energy needed for daily life.

It is important to understand the effects of insulin dosage, eating habits, exercise, and medication on blood glucose levels to improve diabetes control. When using a system, where a real-time continuous blood glucose level monitoring system is connected to an insulin pump, it is possible to manage diabetes better than without a real-time continuous blood glucose level monitoring. With real-time glucose monitoring it is possible to follow blood glucose levels around the clock, discover the effects of diet, exercise, and medication on blood glucose levels, and help prevent too low and too high blood glucose levels. It is obvious that the faster the information about blood glucose level reaches the patient the faster the patient can react and avoid complications for example by injecting insulin to keep blood glucose as near the normal level as possible.

It is obvious that diabetes control is beneficial; Diabetes Control and Complications Trials (DCCT) have showed in 1993 that those patients who kept their blood glucose levels as close to normal as possible had a tremendous decrease in their risk for long-term complications of diabetes. Risk of diabetic eye disease was reduced by 76%, kidney disease by 50%, and nerve disease by 60%.

Portable medical devices having wireless data communication capabilities are especially suitable for continuous diabetes control. These wireless medical devices are deployed in a network to transfer data between two or more separate medical devices.

Current real-time continuous glucose monitoring systems have relatively high power consumption, long response time to changes, the response time for example to changed blood glucose level, being few minutes. Further, for example in case of interference a master device may not get a data packet at all from a slave device and stays in an active state for few minutes longer, waiting the packet from the slave device, which, of course, consumes a great deal of power. In addition, current monitoring systems need bigger devices due to their large power consumption which creates a need for a battery of a relatively large size or for a rechargeable battery.

There is a need for a system comprising portable devices having lower power consumption, shorter response times, more flexible transmitting time periods, and synchronized connection.

SUMMARY OF THE INVENTION

The aim of the present invention is to create a system, including a wireless wrist computer optimized to use a standard battery, for example CR2032 lithium coin battery, using a protocol that enables synchronic, continuous, consistent, and accurate data transfer between devices and having low-power consumption.

It is an object of the present invention to provide an improved data communication method for a wireless medical device network having configured data transfer between the devices using a synchronized data communication protocol.

The method according to the present invention is primarily characterized in what will be disclosed in the characterizing part of claim 1.

DETAILED DESCRIPTION OF THE INVENTION

Figure 2:
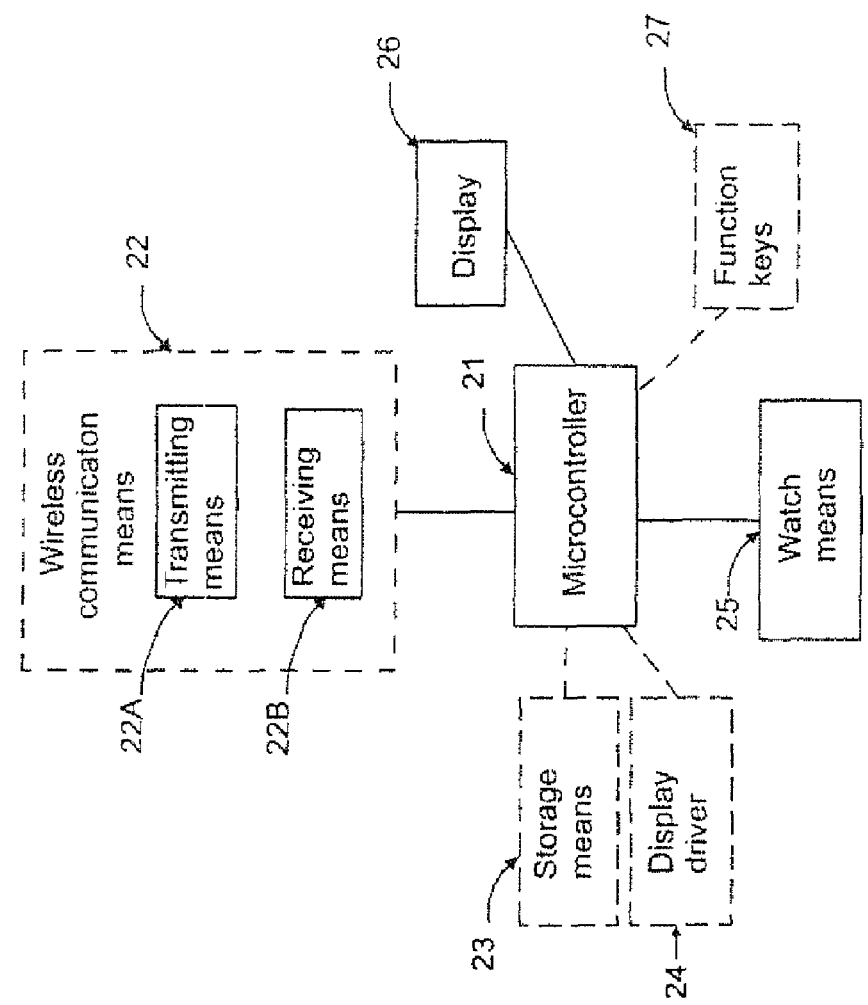
FIG. 2 shows a schematic representation of a wrist computer configured in accordance with an embodiment of the invention.

In an embodiment of the invention, the wireless wrist computer comprises at least a microcontroller, which comprises at least a memory, in which microcontroller at least one computer program can be executed. The computer program comprises control means for controlling and monitoring functions of other devices in the device network. The wireless wrist computer also comprises a display driver, arranged to allow computer programs to interact with a device, a wireless data transmission means, arranged to connect the computer to another device in the network, and a monitor, for transmitting information from the computer to the user.

The term "wireless data transmission means" refers to wireless communication devices such as RF devices and means known as such, e.g. transmitters, receivers, conductors, connectors, antennas, program codes, with the aid of which data communication between the parts of the apparatus can be handled.

There may be several devices in a medical device network. The wrist computer can be connected via a wireless network to a controlled device, such as an insulin pump, a TENS/EMS muscle stimulator, a pain control device, a weight management system or another drug pump, and to a measuring device such as a blood glucose meter, a pulse meter, a physical movement meter, or another device measuring physical activities. In addition, other devices such as a personal computer (PC), a laptop, a database, control units, and a remote control for the controlled device may also be connected to the medical device network.

Control units for transmitting control functions from a user to a computer stand for means through which the user or someone else can control the function of the device. These control units can, for example, be functions keys, buttons of a device or a keyboard. The control units can also be means reacting to voice, e.g. a microphone and voice recognition means. It is also possible that the device receives instructions from external electronic messages, e.g. text messages. In that case the control units comprise means with which they can receive text messages or other messages and the information contained therein.

Desirable RF operating features could be carried out by an embodiment of a communication method for a medical device network comprising wireless devices using a RF data communication protocol, which defines the behaviour of a hardware connection. The use of this RF data communication protocol enables low-power, efficient, and effective transferring of data over wireless links between devices arranged in a network. The two-way medical device network includes a plurality of devices, a master device and at least one slave device configured to communicate data between the devices using a synchronized data communication protocol, arranged in a wireless network. The data represents the desired information to be transferred within the medical device network. In certain embodiments, the wireless signals convey data packets that include the desired data fields, for example, the identification (ID) code of the transmitter device, device status information, physiological patient data, alerts, alarms, information about the next packet to be transmitted and information on the need to change the transmitting period or control parameters in the devices.

In the communication protocol according to the invention one device is defined to be the node of highest priority, and it is called the master device, which acts as a receiver and a transmitter and controls, coordinates and monitors the mutual data communication between all the devices including itself, e.g. the master device defines the communication times for the transmission of the data packets. Other devices in the network are defined to be nodes of lower priority, and they are called as slaves, acting also as a receiver and a transmitter. It is preferred to define a device with the most critical power consumption, such as the wrist computer, as the master device, because when using a long time period the time window, in which the master device needs to be in an active state, can become relatively long due to tolerances of the components. Hence, after a long time period the RF-circuit of the master device needs to be active for longer period of time, which means that the time window needs to be larger and due to this the power consumption becomes higher. The master device can determine the transmitting periods so that the power consumption is as low as possible, for example by avoiding too frequent transmitting times. In an embodiment of the invention, at least in a case of multiple devices, it is preferred to define an insulin pump as a master device, because it needs to communicate with all the devices.

According to this invention it is also possible to reverse a master device and a slave device by redefining the master device to be the slave device, and vice versa during the communication. This is especially useful in a lost signal situation when the synchronization between the devices is lost. In this way, the synchronization could be restored faster and with lower power consumption. In a lost signal situation it is also possible to simply send empty packets containing only information on the transmitting device until the synchronization is restored.

The improved data communication method involves the following steps: defining the master device within a medical device network, defining all slave devices within a medical device network, the master device transmitting a packet intended for the slave device and requesting a data packet, the slave device transmitting the desirable data packet intended for the master device, and the master device transmitting a response packet intended for the slave device. The response packet may also include data for the slave device.

In a preferred embodiment of the invention, a master device and at least one slave device transmit and receive data packets between the devices using the synchronized data communication protocol. According to the protocol the master device is configured to receive data packets from the slave device, and the slave device is configured to transmit data packets intended for the master device. The master device defines a first time period between consecutive packets to be transmitted and a second time period for calculating the number of packets received by the master device during the second time period. In addition, the master device determines a first number of packets to be received by the master device in the predetermined second time period. The master device calculates the number of data packets transmitted from the slave device and received by the master device in the predetermined second time period. In the case of the calculated number of packets is smaller than the determined first number of packets to be received (a first threshold value) the first time period is decreased, and in the case of the calculated number of packets is larger than a determined second number of packets to be received (a second threshold value) the first time period is increased. The determined first and second numbers of packets (the first and the second threshold value) can also be the same values.

The master device may be defined to be a controlled device such as an insulin pump or a wrist computer. There may be a plurality of slave devices, for example, a drug pump, such as an insulin pump, a typical wireless remote control for the drug pump, a measuring device, such as a glucose level monitor, and/or a wrist computer.

The master device, acting as a receiver and a transmitter, transmits a data packet, or in the case of no data, an empty packet, to the slave device, acting as a receiver and a transmitter. The data packet may include for example necessary information such as information on the next packet to be transmitted to the master device, ID information from the device sending this packet, and information indicating when the requested packet should be transmitted to the master device etc. After this, the master device stays in the active state ready to receive the requested data packet (in here a response packet) including a receipt and possible requested data from the slave device. After receiving the packet from the master device the slave device transmits the response packet to the master device. If the slave device does not get the response packet, e.g. due to interference etc., the master device will retransmit the data packet to the slave device until the slave device receives the packet and the master device receives the response packet from the slave device. The next packet to the slave device from the master device includes receipt of the response packet transmitted by the slave device. If the slave device does not receive this receipt in the next packet from the master device, it will retransmit the response packet until the master device receives the response packet and the slave device receives the next packet with receipt from the master device.

In addition, the master device defines the used time periods (in here the term time period refers to the period of time between the active states) according to the data communication protocol, to be multiple of each other, for example if the longest time period is 6 s, the next period would be 3 s and the next 1.5 s and so on. Typically, the longest time period is 2 to 6 s and the shortest 10 ms. The medical device network uses typically 3 to 4 different time periods. It is useful to have multiple time periods due to an interference, in some cases multiple time periods could make the reliability of packet transmitting or receiving better.

It is possible to change the used time period when necessary, for example when there are more packets to be transmitted, the used time period is shorter and vice versa or when there is a need for updated data the used time period is shorter. It is defined in the protocol that in a defined time period a certain number of packets should get across to the master device, if not, the time period of transmitting will be changed shorter, e.g. the transmitting density will then be higher, if yes, the time period of transmitting will be changed longer, e.g. the transmitting density will then be lower.

In addition the size of the packets to be transmitted may be different, which enables the master device to be active for a shorter period of time, which further enables lower power consumption, if the amount of data to be transmitted is small, and respectively in case of a large amount of data the master device is in active state for a longer period of time. The size of the packet is also alterable, for example in a case of a large data packet, it is possible to divide the packet into smaller packets and send them using a short time period.

Due to the adaptable characteristics of the protocol concerning the time period and the size of a packet it is possible to respond to future needs relating to the size of the packets and the process of packet transmitting.

According to the invention, all devices need not be active for communication to be established between some of the devices. It is also possible for each device to begin the data communication and to be defined to act as a master device or a slave device.

It is useful to transmit the data from all devices to the master device for safe keeping, calibration and updating of data and possible transmission to e.g. an external unit like a PC or a database for further data acquisition, storage and processing.

Figure 1:
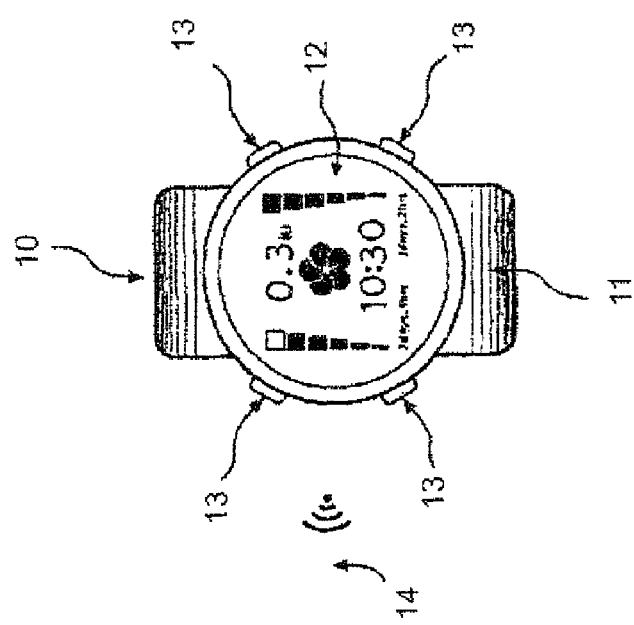
FIG. 1 shows a wrist computer according to an embodiment of the invention.

FIG. 1 shows a wrist computer 10 according to the invention, intended to be attached in a removable manner to the arm of a user e.g. with a wristband 11. The wrist computer can be controlled with function keys 13. A display 12 shows the user the time and variables the wrist watch is arranged to monitor via a data communication network 14 using a data communication protocol. Wireless transmission between the wrist computer and other possible devices in the data communication network is shown schematically with symbol 14.

FIG. 2 shows a schematic functional diagram of a wrist computer 10 according to an embodiment of the invention. The wrist computer consists at least of the following functional blocks: a microcontroller 21, a wireless communication means 22 including transmitting means 22A and receiving means 22B, storage means 23, a display driver 24, a display 26, function keys 27, and watch means 25.

The central functional block is the microcontroller 21, which co-ordinates, monitors and controls the tasks of all the other functional blocks. The microcontroller 21 could be implemented for example by any type of CPU, a microprocessor, an EEPROM or a ROM containing software, etc. The wireless communication means block 22 comprising transmitting means 22A and receiving means 22B is responsible for transmitting and receiving of data. The display 26 is arranged to display the time and relevant information to the patient e.g. the result of a measurement. If desired, the result of the measurement can be stored in the storage means 23 for later retrieval and further be sent to another device in the medical device network e.g. pc through the transmitting means 22A. In addition, at least one computer program can be executed in the storage means 23. The storage means 23 can be for example a standard RAM memory. Sometimes the RAM/ROM of the microcontroller 21 is sufficient and no storage means 23 are needed. The display driver 24 is arranged to allow computer programs to interact with a device and in the case of a wrist computer it is usually integrated in the microcontroller 21. The function keys 27 are not necessary, but when existing they are arranged to control the wrist computer. All these tasks take place under the supervision and coordination of the microcontroller 21. Wrist computer also includes watch means 25 arranged to enable the wrist computer to act as a normal wrist watch as well.

Figure 3:
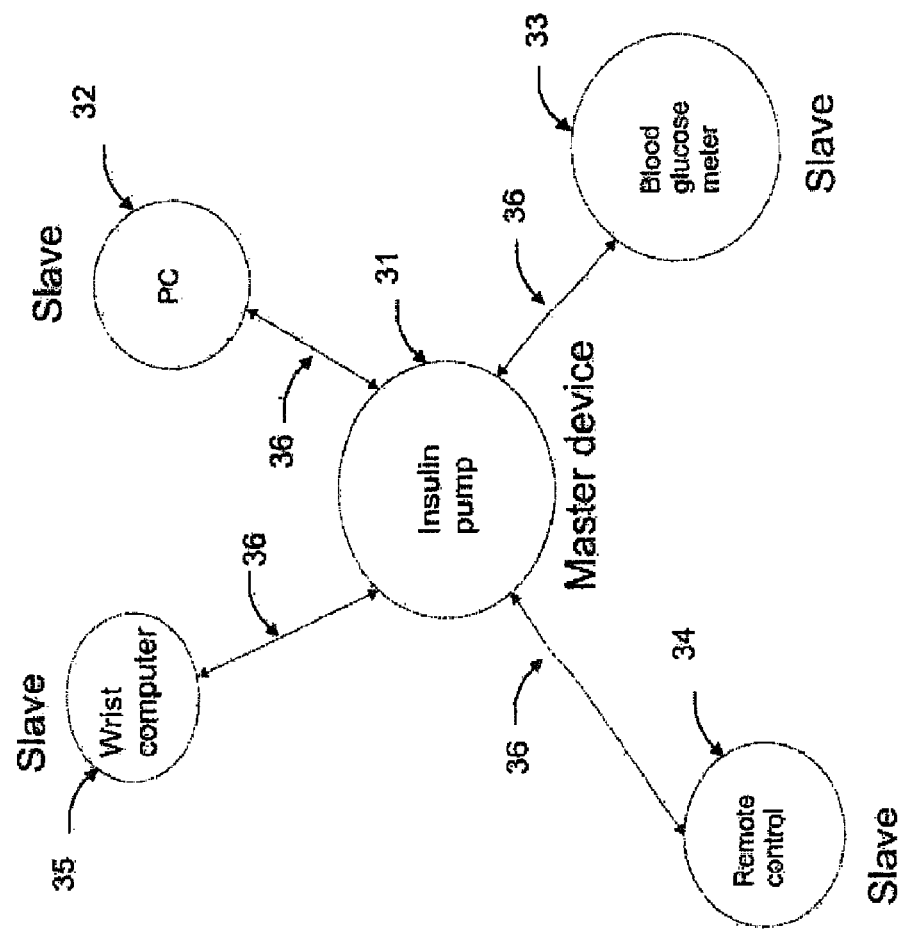
FIG. 3 shows a schematic functional diagram of a medical device network according to an embodiment of the invention.

FIG. 3 shows a schematic functional diagram of a medical device network according to an embodiment of the invention. The master device in this embodiment is an insulin pump 31. The insulin pump 31 is the node responsible for the coordination, supervision and control of the information and data exchange between itself and all the other present and activated nodes, slave devices; a PC 32, a blood glucose meter 33, a wireless remote control 34, and a wrist computer 35. The master device 31 receives and stores the information and data generated in the slave devices 32 to 35 for possible retrieval or transmission to the PC 32 for further storage and processing. The blood glucose meter 33 indicates the glucose level of the blood and transmits it further to the insulin pump 31. The wrist computer 35 can for example act as a sport watch. The insulin pump 31 doses the insulin on the basis of the information transmitted to it. The insulin pump 31 can be placed for example in a belt or attached to the hip of the user. By means of the remote control 34 the usability of the insulin pump 31 can be improved. The programming and monitoring of the pump 31 can be performed by the aid of the remote control 34.

The insulin pump 31 and the blood glucose meter 33 are only provided as examples of a controlled device and measuring device that could be used in accordance with this invention, e.g. any other drug pump or the like can be used as a controlled device and e.g. a pulse meter or the like can be used as a measuring device.

Some of the tasks of the slave devices 32 to 35 could be implemented in the master device 31 and vice versa. In addition, some of the tasks of the slave devices 32 to 35 could be implemented in the other slave devices. For example the remote control 34 can be implemented in the wrist computer 35 and then the function keys 13 shown in FIG. 1 act as controlling keys.

Two-way arrows 36 illustrate the two-way communication between the nodes in the network. All devices in the network are connected to each other via a wireless connection.

Figure 4:
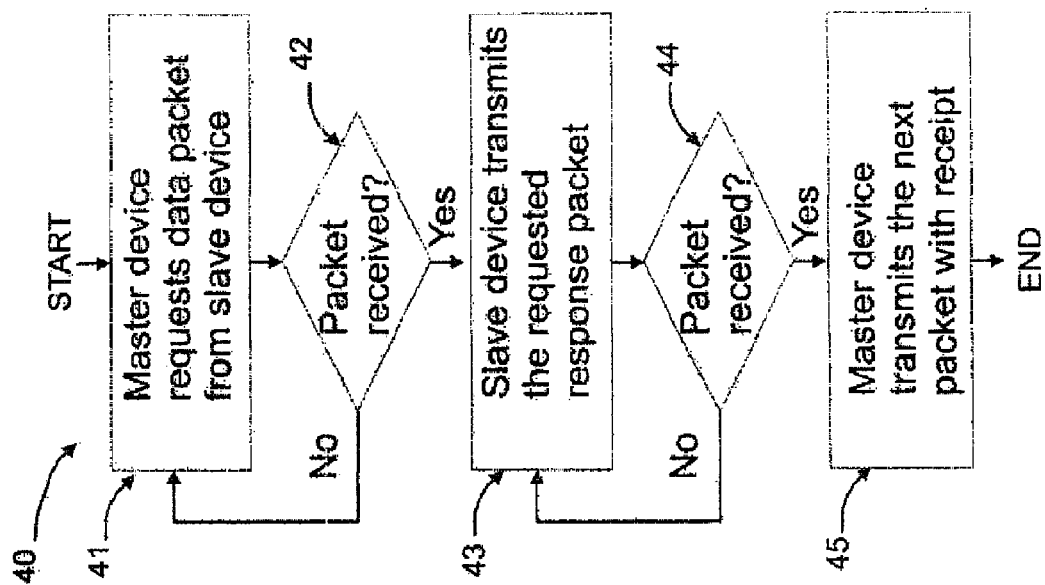
FIG. 4 shows a flowchart illustrating data communication between medical devices in a data communication network.

FIG. 4 shows a flowchart 40 illustrating data communication between medical devices in the data communication network. In the first block 41 the master device, acting as a receiver and a transmitter, transmits a data packet to the slave device, acting as a receiver and a transmitter, and requests a data packet from the slave device. After this, the master device stays in the active state ready to receive the requested data packet (in here a response packet) including a receipt and possible requested data from the slave device. In the block 42 it is determined whether the slave device received the data packet or not. If the slave device received the data packet it will send a response packet to the transmitter. If the slave device did not receive the packet, the master device retransmits the data packet until the slave device receives the data packet from the master device and transmits the response packet or a possible time-out period expires. In the block 43, after receiving the packet from the master device, the slave device sends the response packet to the master device. In the block 44 it is determined whether the master device received the response packet or not. If the master device received the data packet it will send a receipt of it in the next data packet to the slave device, in block 45. If the master device did not receive the response packet, the slave device resends the response packet until the master device receives the response packet from the slave device and transmits the next data packet with the receipt or a possible time-out period expires.

The figures show only a few preferred embodiments according to the invention. The figures do not separately show features that are irrelevant in view of the main idea of the invention, known as such or obvious as such for a person skilled in the art. It is apparent to a person skilled in the art that the invention is not limited exclusively to the examples described above, but the invention can vary within the scope of the claims presented below. The dependent claims present some possible embodiments of the invention, and they are not to be considered to restrict the scope of protection of the invention as such.

The invention claimed is:

1. A wireless data communication system comprising:
   a master device comprising wireless data communication means for transmitting and receiving data packets between the master device and at least one slave device using a synchronized data communication protocol,
   at least one slave device comprising wireless data communication means for transmitting and receiving data packets between the master device and at least one slave device using the synchronized data communication protocol,
   means for monitoring data traffic of a communication channel, from the slave device(s) to the master device, to control the traffic in the channel itself, the means
   defining a first time period between consecutive packets to be transmitted in the master device,
   defining a second time period for calculating the number of packets received by the master device during the second time period,
   calculating the number of data packets received by the master device in the predetermined second time period, wherein
      when the calculated number of packets is smaller than a first threshold value the first time period is decreased, and
      when the calculated number of packets is larger than a second threshold value the first time period is increased,
   wherein monitoring data traffic of the communication channel, from the slave device(s) to the master device, to control the traffic in the channel itself reduces the average power consumption in a wireless data communication system, and
   wherein said monitoring of data traffic reduces data transfer variation and improves consistent data transfer between the master device and the slave device(s).

2. The wireless data communication system according to claim 1, characterised in that the master device is a controlled device or a measuring device.

3. The wireless data communication system according to claim 1, characterised in that the slave device is a controlled device or a measuring device.

4. The wireless data communication system according to claim 1, characterised in that the master device defines communication times for the transmission of the data packets.

5. The wireless data communication system according to claim 1, characterised in that the first threshold value is a determined number of packets to be received by the master device in the predetermined second time period.

6. The wireless data communication system according to claim 1, characterised in that the second threshold value is a determined number of packets to be received by the master device in the predetermined second time period.

7. The wireless data communication system according to claim 1, characterised in that a large data packet is divided into smaller packets and be transmitted by using a time period shorter than the first time period.

8. The wireless data communication system according to claim 1, characterised in that the slave device is defined to be the master device.

9. A method for a wireless data communication comprising:
   transmitting and receiving data between a master device and at least one slave device using a synchronized data communication protocol,
   reducing average power consumption in the wireless data communication system by monitoring data traffic of a communication channel to control the traffic in the channel itself including the sub-steps of:
      defining a first time period between consecutive packets to be transmitted to the master device,
      defining a second time period for calculating the number of packets received by the master device during the second time period,
      calculating the number of data packets received by the master device in the predetermined second time period, wherein
         when the calculated number of packets is smaller than a first threshold value the first time period is decreased, and
         when the calculated number of packets is larger than a second threshold value the first time period is increased, wherein said monitoring of data traffic reduces data transfer variation and improves consistent data transfer between the master device and the slave device(s).

10. The method for a wireless data communication according to claim 9, characterised in that the master device is a controlled device or a measuring device.

11. The method for a wireless data communication according to claim 9, characterised in that the slave device is a controlled device or a measuring device.

12. The method for a wireless data communication according to claim 9, characterised in that the master device defines communication times for the transmission of the data packets.

13. The method for a wireless data communication according to claim 9, characterised in that the first threshold value is a determined number of packets to be received by the master device in the predetermined second time period.

14. The method for a wireless data communication according to claim 9, characterised in that the second threshold value is a determined number of packets to be received by the master device in the predetermined second time period.

15. The method for a wireless data communication according to claim 9, characterised in that a large data packet is divided into smaller packets and transmitted by using a time period shorter than the first time period.

* * * * *